US010687956B2

(12) United States Patent
Ullrich, Jr. et al.

(10) Patent No.: US 10,687,956 B2
(45) Date of Patent: Jun. 23, 2020

(54) CORPECTOMY IMPLANTS WITH ROUGHENED BIOACTIVE LATERAL SURFACES

(71) Applicant: Titan Spine, Inc., Warsaw, IN (US)

(72) Inventors: Peter F. Ullrich, Jr., Neenah, WI (US); Chad J. Patterson, Port Washington, WI (US); Eric Kennedy, Milwaukee, WI (US); Carmie A. Thompson, III, Milwaukee, WI (US)

(73) Assignee: Titan Spine, Inc., Mequon, WI (US)

( * ) Notice: Subject to any disclaimer, the term of this patent is extended or adjusted under 35 U.S.C. 154(b) by 932 days.

(21) Appl. No.: 14/306,460

(22) Filed: Jun. 17, 2014

(65) Prior Publication Data

US 2015/0359639 A1 Dec. 17, 2015

(51) Int. Cl.
*A61F 2/44* (2006.01)
*A61F 2/30* (2006.01)

(52) U.S. Cl.
CPC .......... *A61F 2/442* (2013.01); *A61F 2/30771* (2013.01); *A61F 2/44* (2013.01); *A61F 2/4455* (2013.01); *A61F 2/4465* (2013.01); *A61F 2002/30011* (2013.01); *A61F 2002/3084* (2013.01); *A61F 2002/30112* (2013.01); *A61F 2002/30125* (2013.01); *A61F 2002/30235* (2013.01); *A61F 2002/30451* (2013.01); *A61F 2002/30593* (2013.01); *A61F 2002/30838* (2013.01); *A61F 2002/30906* (2013.01); *A61F 2002/30925* (2013.01)

(58) Field of Classification Search
CPC ...................................................... A61F 2/446
See application file for complete search history.

(56) References Cited

U.S. PATENT DOCUMENTS

| | | |
|---|---|---|
| 6,736,849 B2 | 5/2004 | Li et al. |
| 7,067,169 B2 | 6/2006 | Liu et al. |
| 7,368,065 B2 | 5/2008 | Yang et al. |
| 7,374,642 B2 | 5/2008 | Deutchman et al. |
| 7,445,640 B2 | 11/2008 | Despres, III et al. |
| 7,501,073 B2 | 3/2009 | Wen et al. |
| 7,704,225 B2 | 4/2010 | Kantrowitz |
| 7,771,774 B2 | 8/2010 | Berckmans, III et al. |
| 7,824,462 B2 | 11/2010 | Webster et al. |
| 7,901,462 B2 | 3/2011 | Yang et al. |
| 7,951,285 B2 | 5/2011 | Zipprish |
| 7,972,648 B2 | 7/2011 | Berckmans, III et al. |

(Continued)

FOREIGN PATENT DOCUMENTS

WO 2014018325 1/2014

OTHER PUBLICATIONS

International Search Report and Written Opinion issued in related application PCT/US2015/036118 dated Sep. 23, 2015.

(Continued)

*Primary Examiner* — Samuel S Hanna

(57) ABSTRACT

Implants for vertebral body or functional spinal unit replacement comprise a bioactive surface roughening on one or more of the anterior, posterior, and lateral surfaces of the implant. The bioactive surface includes macro-, micro-, and nano-scale structural features that contact vertebral bone that lines a specialized channel in a vertebrae, and thereby facilitate bone growth and osteointegration of the implant with the vertebral bone.

15 Claims, 10 Drawing Sheets

(56) References Cited

U.S. PATENT DOCUMENTS

| | | |
|---|---|---|
| 8,277,577 B2 | 10/2012 | Garcia et al. |
| 8,309,162 B2 | 11/2012 | Charlton et al. |
| 8,334,044 B2 | 12/2012 | Myung et al. |
| 8,399,008 B2 | 3/2013 | Webster et al. |
| 8,414,908 B2 | 4/2013 | Jin et al. |
| 8,486,319 B2 | 7/2013 | Victor et al. |
| 8,632,836 B2 | 1/2014 | Fredriksson et al. |
| 8,632,843 B2 | 1/2014 | Andersson et al. |
| 8,641,418 B2 | 2/2014 | Mayfield et al. |
| 8,679,517 B2 | 3/2014 | Palmaz |
| 8,696,759 B2 | 4/2014 | Tong et al. |
| 9,421,053 B2 | 8/2016 | Kennedy et al. |
| 2003/0181980 A1 | 9/2003 | Berry et al. |
| 2004/0049270 A1 | 3/2004 | Gewirtz |
| 2006/0004466 A1 | 1/2006 | Glocker et al. |
| 2006/0241760 A1* | 10/2006 | Randall .................. A61F 2/447 623/17.11 |
| 2007/0259427 A1 | 11/2007 | Storey et al. |
| 2008/0160259 A1 | 7/2008 | Nielson et al. |
| 2008/0208351 A1 | 8/2008 | Besenbacher et al. |
| 2008/0262623 A1 | 10/2008 | Bagga et al. |
| 2009/0283701 A1 | 11/2009 | Ogawa |
| 2010/0076559 A1 | 3/2010 | Bagga et al. |
| 2010/0204777 A1 | 8/2010 | Storey et al. |
| 2011/0089041 A1 | 4/2011 | Gupta et al. |
| 2011/0282454 A1* | 11/2011 | Ullrich, Jr. ............ A61F 2/4465 623/17.16 |
| 2011/0287223 A1 | 11/2011 | Victor et al. |
| 2012/0022650 A1 | 1/2012 | Gilbert et al. |
| 2012/0239150 A1 | 9/2012 | Ullrich, Jr. et al. |
| 2012/0276336 A1 | 11/2012 | Malshe et al. |
| 2012/0312778 A1* | 12/2012 | Ullrich, Jr. ............ A61F 2/4455 216/41 |
| 2012/0316651 A1 | 12/2012 | Ullrich, Jr. et al. |
| 2012/0316653 A1* | 12/2012 | Ullrich, Jr. ............ A61F 2/4465 623/17.16 |
| 2013/0006363 A1 | 1/2013 | Ullrich, Jr. et al. |
| 2013/0045360 A1 | 2/2013 | Ibacache et al. |
| 2013/0059946 A1 | 3/2013 | Zhu et al. |
| 2013/0110243 A1 | 5/2013 | Patterson et al. |
| 2013/0244003 A1 | 9/2013 | Yoo et al. |
| 2013/0248487 A1 | 9/2013 | Mayfield et al. |
| 2013/0261764 A1 | 10/2013 | Guerra et al. |
| 2013/0292357 A1 | 11/2013 | Ullrich, Jr. et al. |
| 2013/0302427 A1 | 11/2013 | Arvidsson et al. |
| 2013/0302509 A1* | 11/2013 | McEntire .............. A61L 27/025 427/2.24 |
| 2013/0306591 A1 | 11/2013 | Ullrich, Jr. et al. |
| 2013/0310938 A1 | 11/2013 | Sournac |
| 2013/0330688 A1 | 12/2013 | Hedrick et al. |

OTHER PUBLICATIONS

Examination Report No. 1, dated Feb. 13, 2019, for Australian Patent Application No. 2015277294.

* cited by examiner

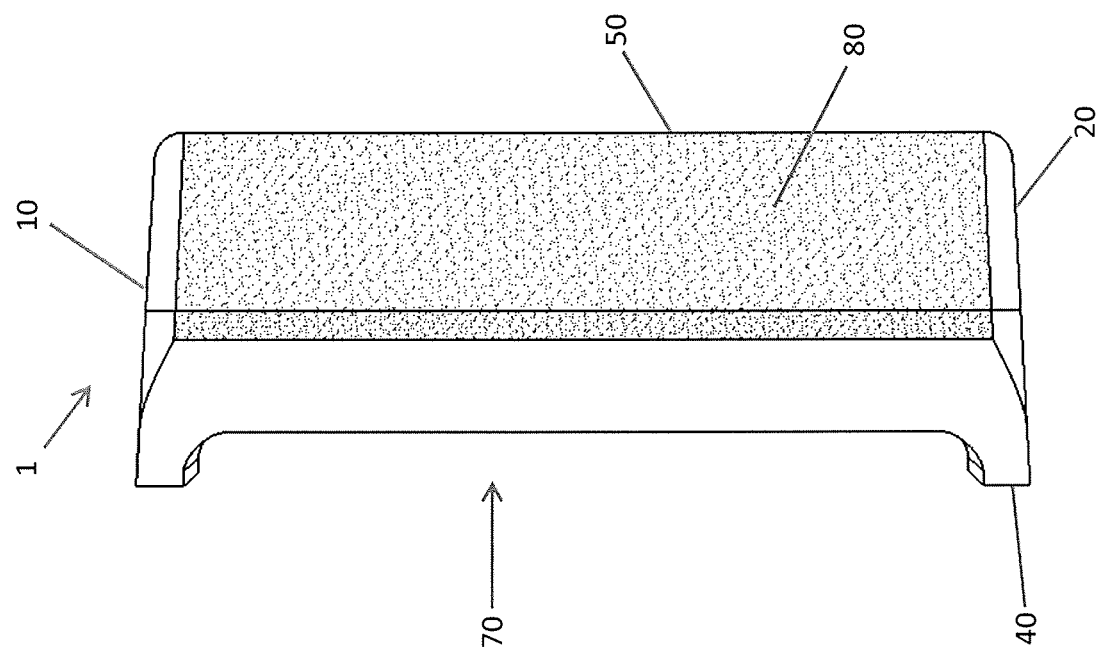
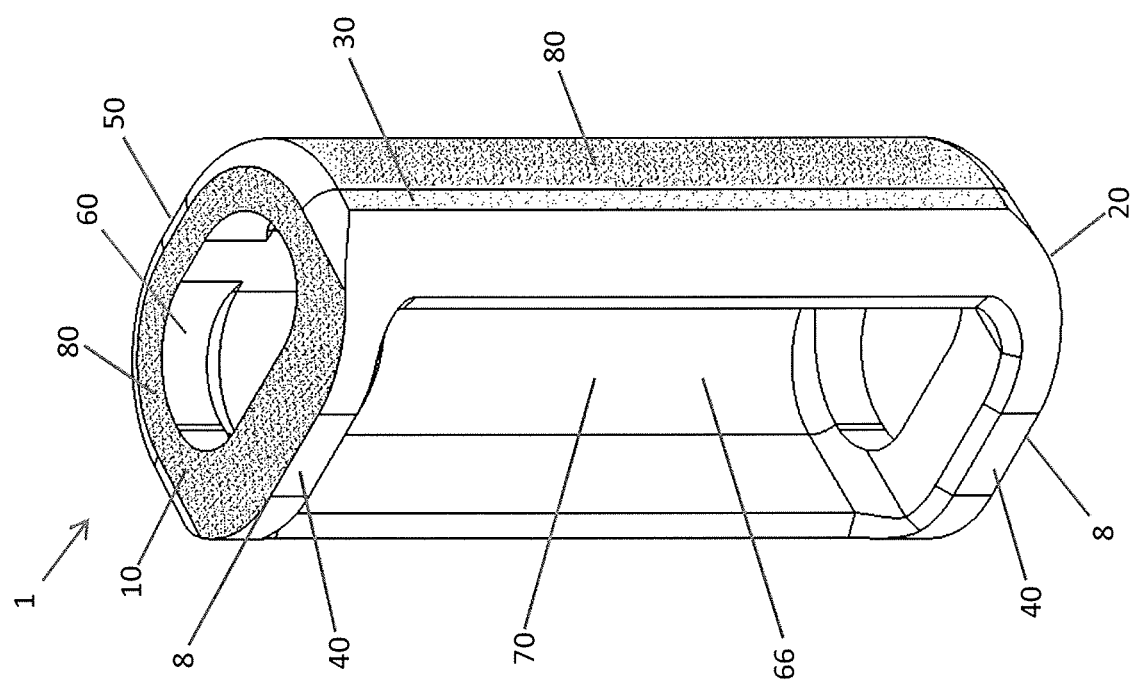

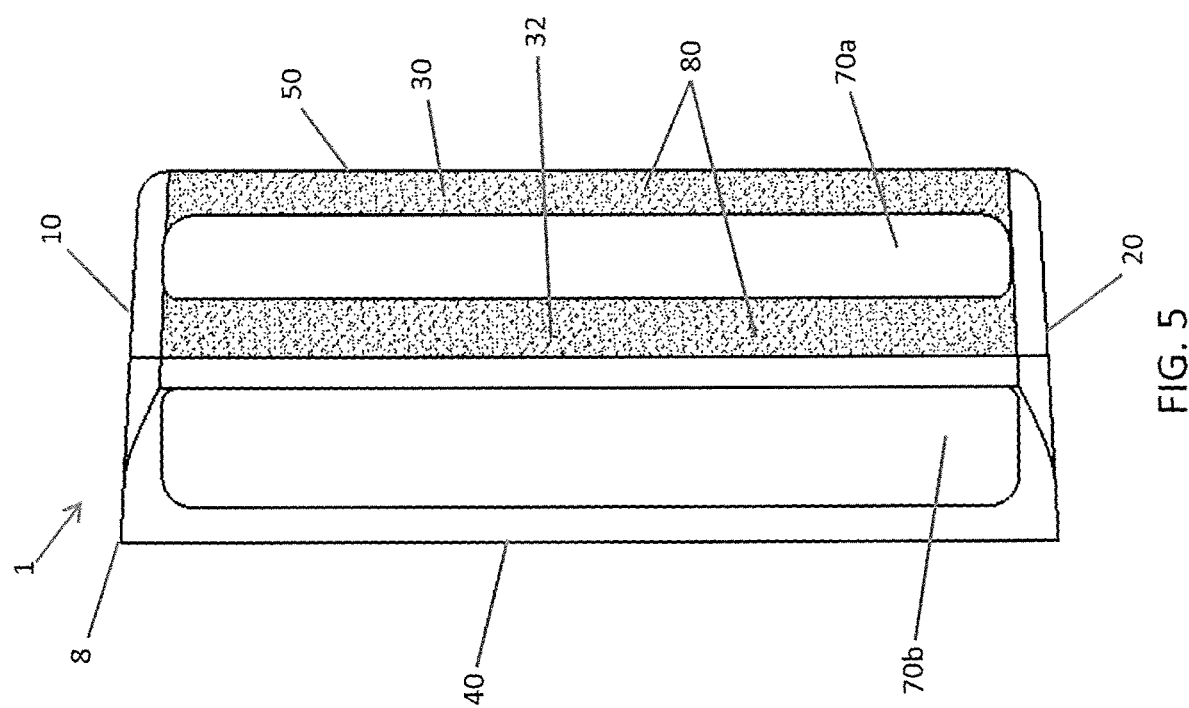

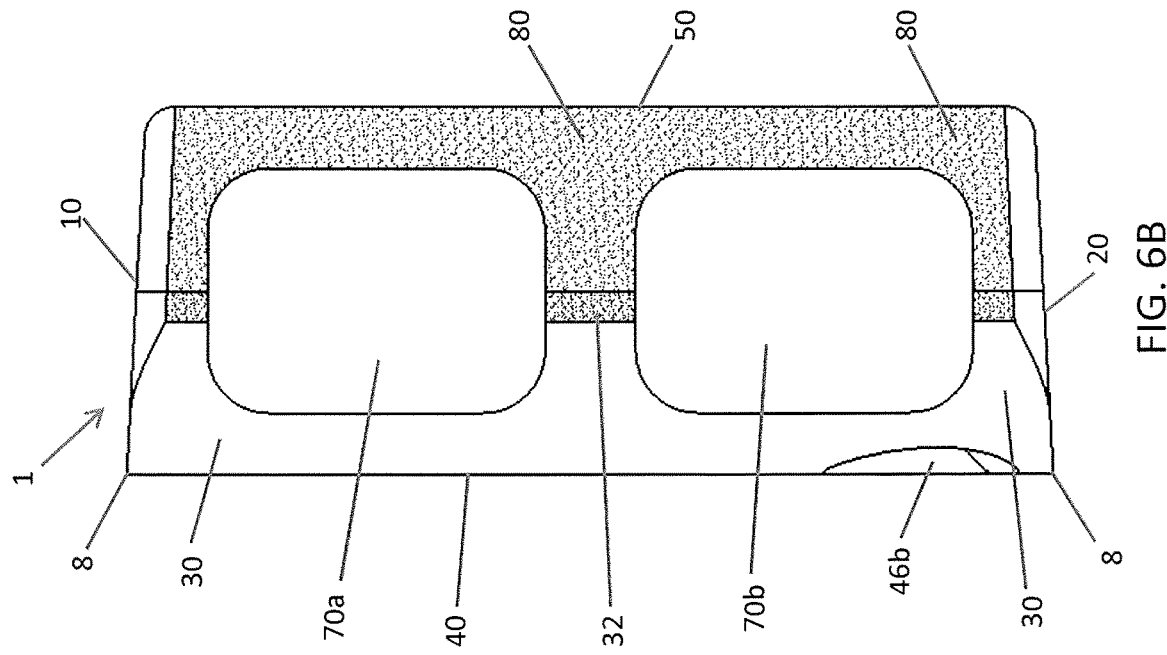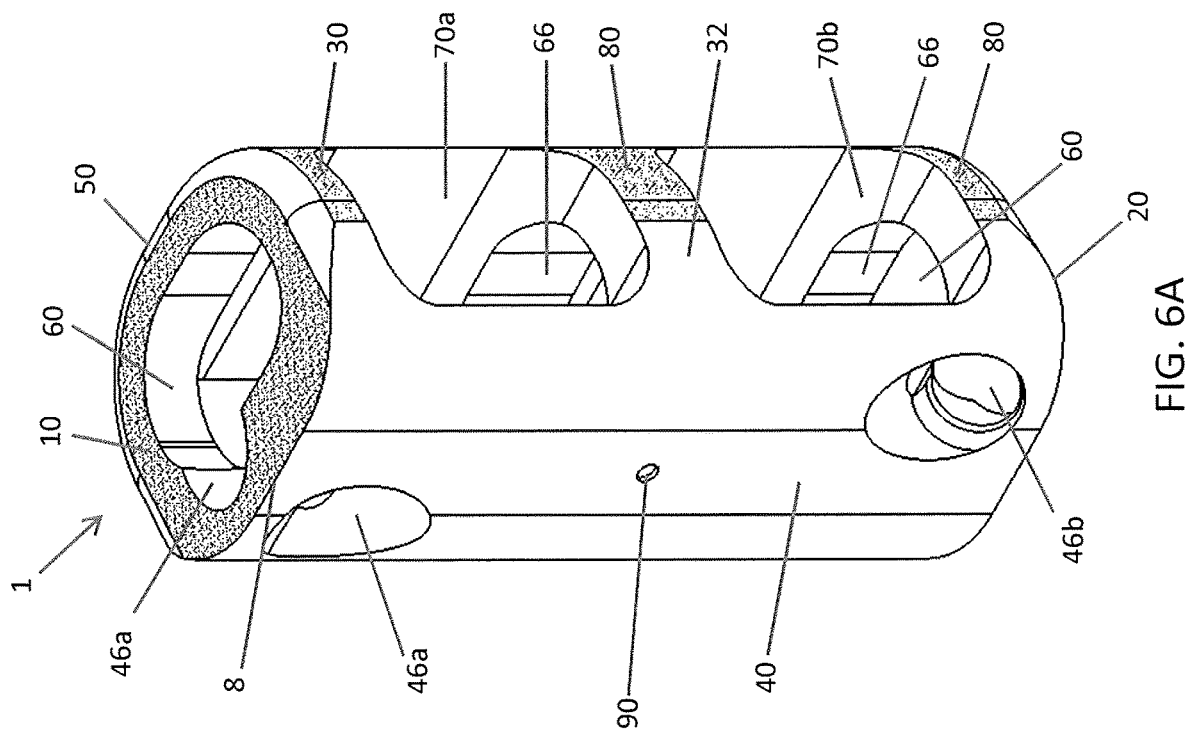

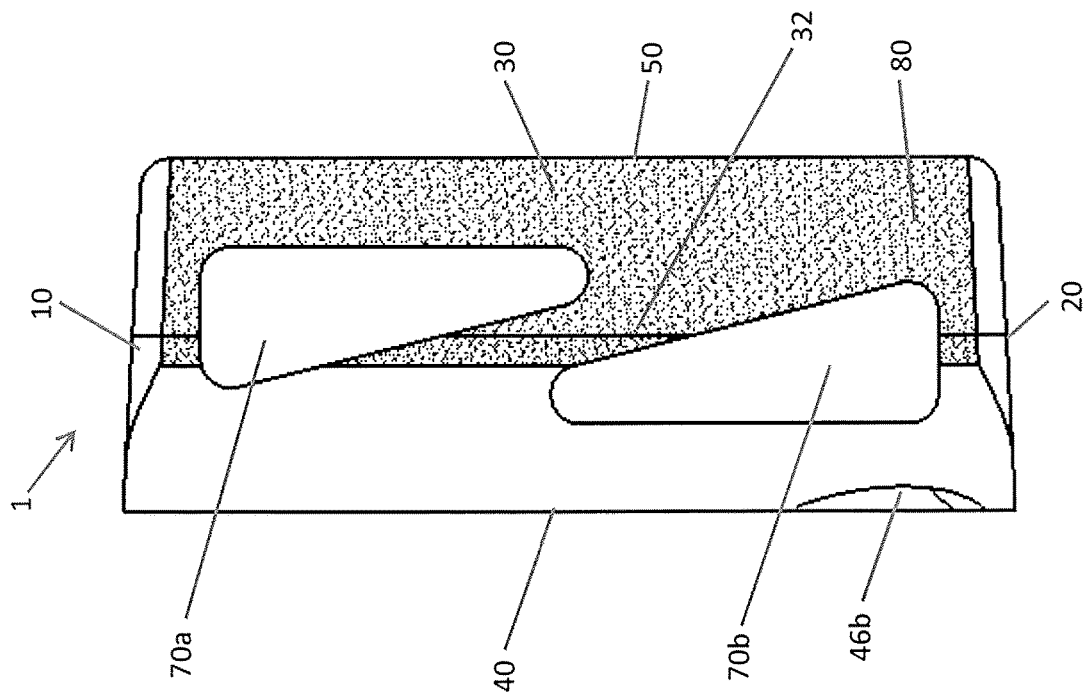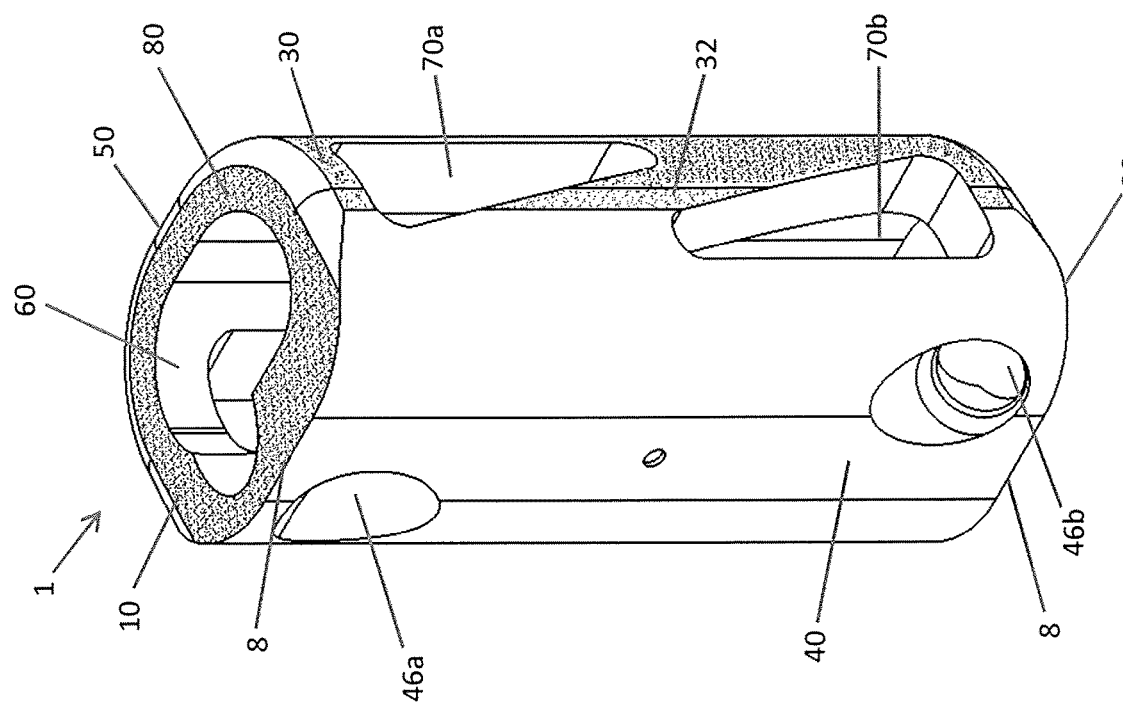

Ra = Average (1, 4, 6, 8, 5, 2, 1, 4, 1, 2, 1, 4, 7, 4, 1, 2, 5, 8, 2, 1, 4, 1, 1)

Ra = 3.26

CORPECTOMY IMPLANTS WITH ROUGHENED BIOACTIVE LATERAL SURFACES

FIELD OF THE INVENTION

The invention relates generally to implants for vertebral body or functional spinal unit replacement. More particularly, the invention relates to such implants that have a bioactive surface roughening on at least bone-contacting portions of the sides, and methods for implanting such implants. The bioactive surface roughening promotes osteogenesis and osteointegration about the lateral surfaces of the implant.

BACKGROUND OF THE INVENTION

Various publications, including patents, published applications, technical articles and scholarly articles are cited throughout the specification. Each of these cited publications is incorporated by reference, in its entirety and for all purposes, in this document.

The spinal column includes vertebrae and discs stacked together, and an interior pathway through which the spinal cord extends. The vertebrae provide the support and structure of the spine. The discs, located between the vertebrae, act as cushions and contribute to the flexibility and motion of the spinal column. Two adjacent vertebrae and an intervening disc are known in the art as a functional spinal unit or spinal motion segment. In case of damage or degenerative disease, including cancer, to the vertebrae or to a functional spinal unit, the injured vertebrae or unit may be removed, in part or in total. The removal procedure is known in the art as a corpectomy. An implant is then inserted in place of the removed vertebrae, unit, or part thereof. Given the large gap that the implant spans, and given that corpectomy procedures typically do not retain much, if any, intervening bone between extant vertebrae, such implant designs generally have not been geared toward encapsulation of the implant with new bone. In addition, new bone growth on and near the implant is often slow, insufficient, and/or uneven, which may lengthen the healing process or diminish the ultimate effectiveness of the procedure. Therefore, it is desirable to enhance bone growth on and around the implant, particularly where the implant stands in place of removed bone material.

SUMMARY OF THE INVENTION

The disclosure features implants, which are implanted into a channel cut through the end plate bone of a vertebrae, in order to replace the removed bone and/or to replace a functional spinal unit. The implants comprise a body that preferably is generally oval-shaped in transverse cross section, and have a height (from the bottom surface to the top surface) that is substantially the same as the height of the vertebral end plate, the vertebral body, or the functional spinal unit the implant replaces. The implants comprise a top surface, a bottom surface, opposing lateral sides, and opposing anterior and posterior sides, with a substantially hollow center in the interior of the implant. The implants also comprise a single vertical aperture, which extends from the top surface to the bottom surface, and is in communication with the substantially hollow center. The vertical aperture has maximum width at its center, and defines a transverse rim on the top surface and on the bottom surface. The transverse rim has a posterior thickness greater than an anterior thickness, and has a blunt and radiused portion along the top of each lateral side and the top of the posterior side. The blunt and radiused portion may taper, particularly at the posterior side. The implants also comprise a bioactive surface roughening. The bioactive roughened surface comprises macro-, micro-, and nano-scale structures capable of facilitating bone growth. This roughening is present on at least the portion of the transverse rim that is not blunt and radiused, the posterior side (substantially all of the posterior side between the top surface and the bottom surface), and at least a portion of each opposing lateral side (between the top surface and the bottom surface), which portion of the lateral side may extend part-way or substantially all the way between the posterior side and the anterior side. Preferably, the blunt and radiused portion does not include any bioactive roughened surface, and the body has a sharp edge at the junction of the anterior side and the top surface and at the junction of the anterior side and the bottom surface. The body may also have a sharp edge at the junction of the anterior side of the single vertical aperture and the top surface, and at the junction of the anterior side of the single vertical aperture and the bottom surface. The implant may comprise a lordotic angle.

The implant may be constructed of any suitable material, including a metal or polymer, or a composite of a metal and polymer. The metal may comprise titanium or an alloy thereof. The polymer may comprise polyetherether-ketone or ultra-high molecular weight polyethylene.

In some aspects, the implant comprises a bone graft material in the substantially hollow center. The bone graft material may comprise cancellous autograft bone, allograft bone, demineralized bone matrix (DBM), porous synthetic bone graft substitute, bone morphogenic protein (BMP), or combinations thereof. In some aspects, the implant comprises one or more screw apertures extending through the anterior side and top surface and through the anterior side and bottom surface.

The implant preferably comprises one or more transverse apertures through the sidewalls of the body, which apertures are in communication with the substantially hollow center. The one or more transverse apertures may be present on the anterior side, the posterior side, and/or one or more of the opposing lateral sides. One or more of the transverse apertures may comprise one or more intermediate walls that divide the transverse apertures. The one or more intermediate walls may be vertically-oriented, horizontally-oriented, and/or diagonally-oriented. The intermediate walls may, but need not, divide the transverse apertures into equally sized transverse apertures.

The disclosure also features methods. The methods comprise implanting an implant, such as any implant described or exemplified herein into a channel through a vertebral body such that the bioactive roughened surface on the posterior side, anterior side, and/or opposing lateral side(s) contacts the remaining vertebral bone that at least partially surrounds the channel. If the implant includes a transverse aperture, the methods may further comprise adding or loading a bone graft material into the substantially hollow center, for example, through the transverse aperture. Preferably, the bone graft material extends through the transverse aperture and makes contact with the vertebral bone that surrounds the channel and the implant inserted into the channel.

BRIEF DESCRIPTION OF THE DRAWINGS

The invention is best understood from the following detailed description when read in connection with the accompanying drawings, in which like reference numbers refer to like elements throughout the various figures. It is emphasized that, according to common practice, the various features of the drawings are not to scale. On the contrary, the dimensions of the various features are arbitrarily expanded or reduced for clarity. Included in the drawings are the following figures in which:

FIG. 4A shows an anterior-lateral view of an implant comprising an anterior window and a bioactive surface roughening on the posterior and lateral sides;

FIG. 4B shows a lateral view of the implant shown in FIG. 4A;

FIG. 5 shows a lateral view of an implant comprising a vertically bifurcated lateral window and bioactive surface roughening on the posterior and lateral sides;

FIG. 6A shows an anterior-lateral view of an implant comprising a horizontally bifurcated lateral window and bioactive surface roughening on the posterior and lateral sides;

FIG. 6B shows a lateral view of the implant shown in FIG. 6A;

FIG. 7A shows an anterior-lateral view of an implant comprising a diagonally bifurcated lateral window and bioactive surface roughening on the posterior and lateral sides;

FIG. 7B shows a lateral view of the implant shown in FIG. 7A;

FIG. 12 graphically represents the total peak-to-valley of waviness of profile macro-, micro-, or nano-scale surface features and structure; and.

DETAILED DESCRIPTION OF THE INVENTION

Various terms relating to aspects of the present disclosure are used throughout the specification and claims. Such terms are to be given their ordinary meaning in the art, unless otherwise indicated. Other specifically defined terms are to be construed in a manner consistent with the definition provided in this document.

As used throughout, the singular forms "a," "an," and "the" include plural referents unless expressly stated otherwise.

The terms subject and patient are used interchangeably. A patient may be any animal, including mammals such as companion animals, laboratory animals, and non-human primates. Human beings are preferred.

A functional spinal unit includes a vertebrae and the intervertebral discs between a superior and inferior vertebrae. A functional spinal unit may include a cervical functional spinal unit, a thoracic functional spinal unit, or a lumbar functional spinal unit.

Figure 1:
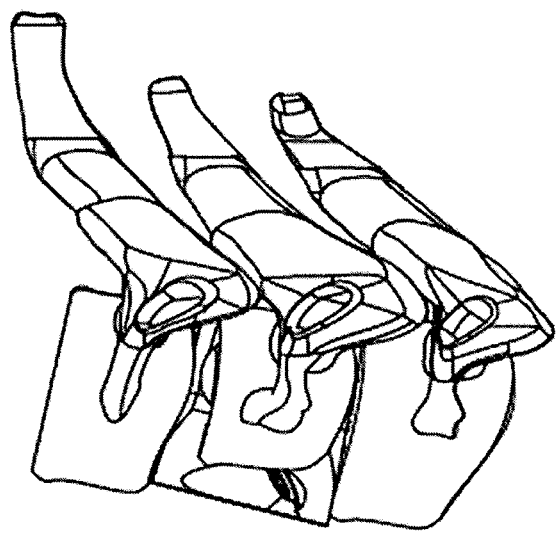
FIG. 1 shows a representation of a functional spinal unit.

Implants in accordance with certain aspects of the disclosure stand in the place of at least a portion of at least one vertebrae, including in the place of a functional spinal unit (FIG. 1). The implants are preferably used in accordance with surgical procedures that retain some portion of a vertebrae (FIG. 2A and FIG. 2B) such that the implant may be seated in place of the removed portion and contact the extant bone, while the top and bottom surfaces of the implant contact the inferior and superior surfaces of adjacent vertebrae, including vertebral end plate bone.

The implants may be made of any suitable material. Suitable materials include plastics, polymers, silicone, metals, ceramics, bone, or composites of any such materials. Suitable polymers include polyether ether ketone (PEEK) and ultra-high molecular weight polyethylene (UHMWPE), as well as urethane dimethacrylate (DUDMA)/tri-ethylene glycol dimethacrylate (TEDGMA) blended resin. Suitable metals may comprise titanium, an alloy of titanium such as an aluminum and vanadium alloy of titanium (e.g., 6-4), a nickel alloy of titanium such as nitinol, a cobalt chromium alloy, or surgical grade steel.

Referring now to the drawing, in which like reference numbers refer to like elements throughout the various figures that comprise the drawing, FIGS. 3A through 7B show various embodiments of an implant 1. The implant 1 includes an elongate body having a top surface 10, a bottom surface 20, opposing lateral sides 30, and opposing anterior 40 and posterior 50 sides. The height of the body may vary, for example, according to the height of the vertebrae and/or functional spinal unit being replaced.

Without being limited to any particular theory or mechanism of action, it is believed that the cumulative effects of at least implant composition, implant surface energy, and implant surface roughness play a major role in the biological response to, and osteointegration of an implant device. Thus, implant fixation may depend, at least in part, on the attachment and proliferation of osteoblasts and like-functioning cells upon surfaces of the implant 1. It is believed that cells attach more readily to relatively rough surfaces rather than smooth surfaces. In this manner, a surface may be bioactive due to its ability to facilitate cellular attachment and osteointegration. The roughened bioactive surface 80 may better promote the osteointegration of the implant 1. On certain faces of the implant 1, the roughened bioactive surface 80 may also better grip the vertebral endplate surfaces and inhibit implant migration of the implant 1 upon placement and seating in a patient. Accordingly, the implant 1 further includes the roughened bioactive surface 80 on one or more bone-contacting portions of the implant 1, including at least a portion of its top 10 and bottom 20 surfaces for gripping vertebral endplate bone of adjacent vertebrae that flank the implant 1, and at least a portion of one or more of the opposing lateral sides 30, anterior 40 side, and posterior 50 side.

The implant 1 includes a vertical aperture 60, which passes through the top 10 and bottom 20 surfaces, and is in communication with a substantially hollow center 66. The shape of the vertical aperture 60 may vary. For example, the shape may be substantially circular, elliptical, or D-shaped. The vertical aperture 60 preferably comprises maximal width at its center. The vertical aperture 60, in combination with the edges around the periphery of the top 10 and bottom 20 surfaces, defines a transverse rim.

The transverse rim has a generally large surface area and contacts the vertebral endplate. The transverse rim may act to better distribute contact stresses upon the implant 1, and hence minimize the risk of subsidence while maximizing contact with the apophyseal supportive bone. The transverse rim may have a variable width, including a larger posterior width than anterior width, or vice versa. It is also possible for the transverse rim to have a substantially constant width around the perimeter of the vertical aperture 60.

One or more of the anterior side 40 edges, posterior side 50 edges, and/or lateral side 30 edges of the implant 1 may be blunt, radiused, rounded and/or tapered (see, e.g., FIG. 3A through FIG. 7B). The blunt and radiused edges are preferably present on at least the insertion face of the implant 1. The rounding, tapering, and blunting may facilitate insertion of the implant 1 by lessening friction or the possibility of snagging vertebral endplate bone as the implant 1 is placed and positioned in the spinal column. As well, the rounding, tapering, and blunting may help to avoid snagging or damaging blood vessels and nerves in and around the insertion site.

The vertical aperture 60 comprises a maximum width at its center. The width of the vertical aperture 60 may range from about 20% to about 80% of the distance between opposing lateral sides. In some aspects, the width ranges from about 40% to about 80% of the distance between the opposing lateral sides. In some aspects, the width ranges from about 50% to about 70% of the distance between the opposing lateral sides. In some aspects, the width ranges from about 50% to about 65% of the distance between the opposing lateral sides. In some aspects, the width ranges from about 60% to about 70% of the distance between the opposing lateral sides. In some aspects, the width ranges from about 55% to about 75% of the distance between the opposing lateral sides. In some aspects, the width ranges from about 60% to about 80% of the distance between the opposing lateral sides. In some aspects, the width is about 40%, about 45%, about 50%, about 55%, about 60%, about 65%, about 70%, about 75%, about 80%, about 85%, or about 90% of the distance between the opposing lateral sides. Preferably, the width of the vertical aperture 60 comprises the dimension between the lateral sides 30.

The top surface 10 and bottom surface 20 may comprise a sharp, expulsion-resistant edge 8. The sharp edge 8 is preferably present at the edge of the anterior side 40, and a sharp edge 8 may also be present at the anterior edge of the vertical aperture 60 on the top surface 10 and bottom surface 20. The sharp edge 8 helps to engage vertebral endplate bone, and inhibit expulsion of the implant 1 following implantation.

Figure 3C:
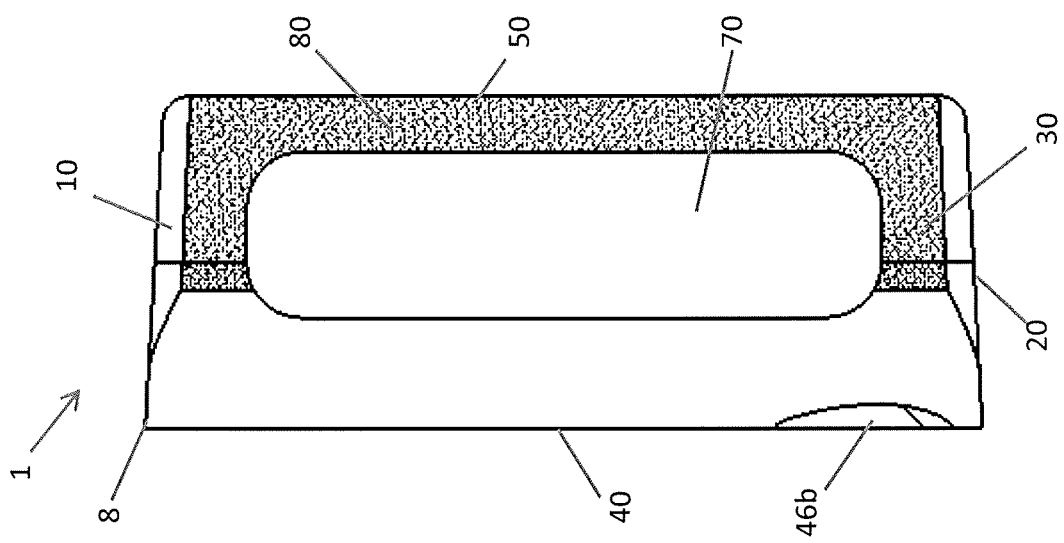
FIG. 3C shows a lateral view of the implant shown in FIG. 3A.
Figure 3B:
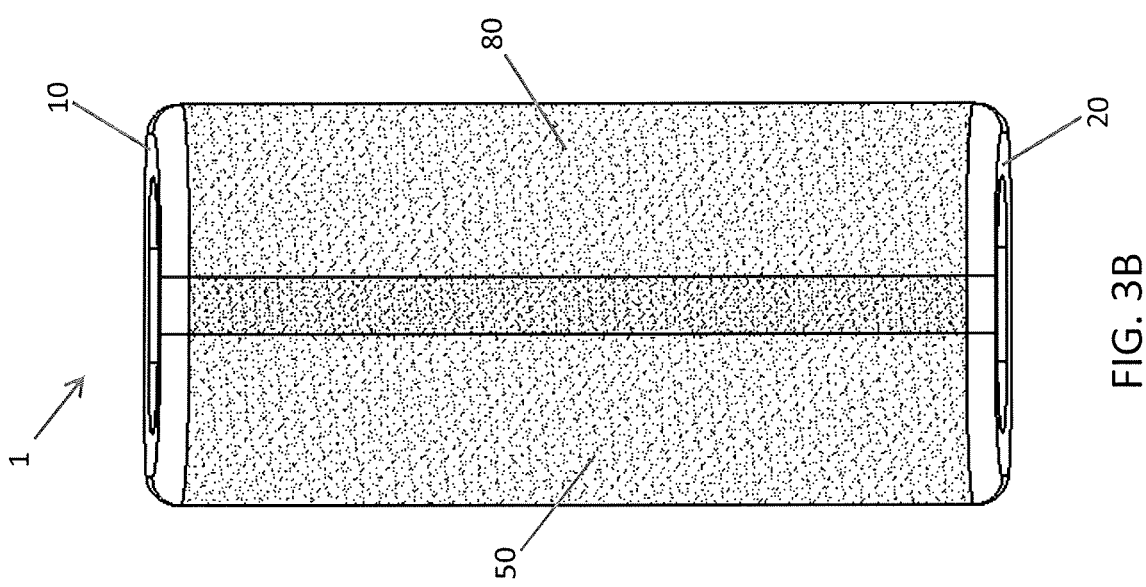
FIG. 3B shows a posterior view of the implant shown in FIG. 3A.
Figure 3A:
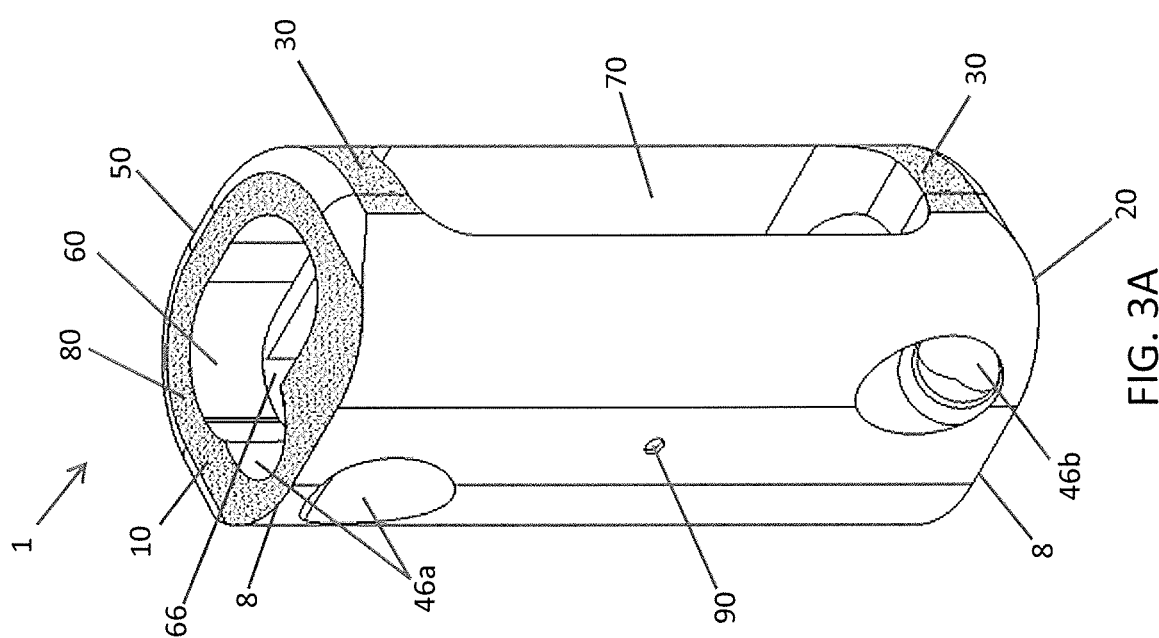
FIG. 3A shows an anterior-lateral view of an implant comprising a lateral window and bioactive surface roughening on the posterior and lateral sides.

The body of the implant 1 may comprise solid anterior 40, posterior 50, or lateral 30 walls. See FIGS. 3B and 4B. The solid wall may comprise substantially the entire height of the implant 1 body. Thus, the solid wall essentially closes the anterior side 40, posterior side 50, or lateral sides walls 30 of the implant 1. The solid wall may offer one or more of several advantages, including reinforcement of the implant 14- and improved bone graft containment. In the cervical applications, for example, it may be important to prevent bone graft material from entering the spinal canal. Though solid, the solid wall may comprise one or more screw apertures 46 (discussed below) and one or more openings 90 (discussed below), for example, as shown in FIGS. 3A, 6A, and 7A.

The implant 1 may include at least one transverse aperture 70. The at least one transverse aperture 70 may be present on one or more of the lateral sides 30 (FIGS. 3A and 3B), or the anterior side 40 (FIG. 4A), or the posterior side 50 (not shown). The at least one transverse aperture 70 preferably passes through the sidewalls of the implant 1 such that the transverse aperture 70 is in communication with the hollow center 66. The at least one transverse aperture 70 may extend a majority of the height of the implant 1. The size and shape of the transverse aperture 70 comprises dimensions to maximize the strength and structural integrity of the implant 1. Suitable shapes for the transverse aperture 70 may be a substantially circular, elliptical, D-shaped, triangular, quadrilateral, rectangular, or polygonal shape. The transverse aperture 70 may be used to fill the hollow center 66 of the implant 1 with a bone graft material, or to add additional bone graft material when the implant 1 is set in position during the implantation procedure. Once the hollow center is filled, the bone graft material may flow out from the vertical aperture 60, as well as one or more of the transverse apertures 70.

In some aspects, each transverse aperture 70 may be divided into at least two separate sections (e.g., 70a and 70b) by an intermediate wall 32. FIG. 5 shows a vertically-oriented intermediate wall 32, FIG. 6A and FIG. 6B show a horizontally-oriented intermediate wall 32, and FIG. 7A and FIG. 7B show a diagonally-oriented intermediate wall 32. The intermediate wall 32 is preferably integral with the implant body. The intermediate wall 32 may offer one or more of several advantages, including reinforcement of the implant 1 and improved bone graft containment.

In some aspects, the implant 1 comprises one or more screw apertures 46. For example, as shown in FIGS. 3A, 6A, and 7A, the implant 1 may comprise a screw aperture 46a near the top of the anterior side 40 and a screw aperture 46b near the bottom of the anterior side 40. The one or more screw apertures 46 may also be present on one or more of the lateral sides 30 (not shown) or on the posterior side 50 (not shown). The one or more screw apertures 46 may comprise screw threads.

The one or more screw apertures 46 essentially bore through the sidewalls of the implant 1 at an angle that would allow a bone screw (not shown) to pass through the implant 1 body and into adjacent bone, not unlike "toenailing" used in carpentry. The bone screw assists in affixing the implant 1 in place within the spinal column, and enhances implant 1 retention and inhibits movement and expulsion of the implant 1 after implantation. Each screw aperture 46 may comprise concave sidewalls to accommodate a screw and fixation collar, for example, the screw and fixation collar described in U.S. patent application Ser. No. 14/272,557, incorporated by reference herein.

In some aspects, the one or more screw apertures 46 and the corresponding insertion path of the screws (not shown) are positioned at an angle of about 30° to about 60° of the vertical axis of the implant 1. Angles less than about 30° or greater than about 60° may be used in some aspects. The degree of angling may be a function of the implant size or type, or of particular patient characteristics, or of the location or position of the implant 1 once implanted. In some aspects, the implant 1 comprises one or more screw apertures 46 configured for the screw to extend through the top 10 and embed in the upper vertebrae, or through the bottom 20 and embed in the lower vertebrate. The one or more screw apertures 46 may be in communication with the hollow center 66 and the vertical aperture 60 on the top 10 or bottom 20 of the implant 1, for example, as shown in FIGS. 3A, 6A, and 7A.

The implant 1 may comprise a lordotic angle, e.g., may be wedge-shaped to facilitate sagittal alignment. Thus, for example, the anterior side 40 of the implant 1 may comprise a height that is larger than the height of the posterior side 50, or vice versa. Alternatively, one of the lateral sides 30 of the implant 1 may comprise a height that is larger than the height of the opposing lateral side 30. The lordotic angle may closely approximate, or otherwise is substantially the same as, the angle of lordosis of the spine of the patient where the implant will be implanted. The implant 1 may have a lordotic angle L about 3%, about 3.3%, about 3.5%, about 3.7%, about 4%, about 4.3%, about 4.5%, about 4.7%, or about 5% greater than the patient's angle of lordosis, though percentages greater than 5% or lesser 3% are possible.

The implant 1 may also comprise an opening 90 in the anterior side 40 (FIGS. 3A, 6A, and 7A), the posterior side 50 (not shown) or one or more of the lateral sides 30 (not shown). The opening 90 may facilitate manipulation of the implant 1 by the practitioner. Thus, a surgical tool (not shown) may be inserted into the opening 90 and, through the engagement between the surgical tool and the opening 90 the implant 1 may be maneuvered. The opening 90 may comprise screw threads to enhance the engagement with the tool.

Except for certain faces, the implant 1 surfaces have heavily rounded edges, creating a low stress contact with the end-plates. The wide rim of the top 10 and bottom 20 surfaces, in contact with the end-plates, creates a low-stress contact due to the large surface area. As well, the implant 1 has an engineered stiffness to minimize the stiffness mismatch with the vertebral body which it contacts. Generally, the implant 1 is shaped to maximize contact with the apophyseal rim of the vertebral endplates. The implant 1 is designed to be impacted between the endplates, with fixation to the endplates created by an interference fit and annular tension. Thus, the implant 1 is preferably shaped and sized to spare the vertebral endplates and leave intact the hoop stress of the endplates. A wide range of sizes are possible to capture the apophyseal rim, along with a broad width of the peripheral rim, especially in the posterior region. It is expected that such designs will lead to reduced subsidence. The implant 1 preferably allows for deflection of the endplates like a diaphragm. A bone graft material inside the implant 1 may receive a load, leading to healthy fusion. The vertical load in the human spine is transferred through the peripheral cortex of the vertebral bodies. By implanting an apophyseal-supporting implant 1 the natural biomechanics may be better preserved than for conventional devices.

The top 10 and bottom 20 surfaces of the implant 1 generally contact vertebral end-plates, for example, at the peripheral apophyseal rim, where the end-plates are the strongest and least likely to subside. It is preferred that the top 10 and bottom 20 surfaces do not include teeth, spikes, or ridges that may score or damage the bone. Rather, the top 10 and bottom 20 surfaces include a bioactive surface roughening 80, also referred to as a roughened surface topography 80, which helps to facilitate osteointegration (e.g., formation of a direct structural and functional interface between the artificial implant and living bone or soft tissue) with the surrounding living bone. Without intending to be limited to any particular theory or mechanism of action, it is believed that these cells attach more readily to relatively rough surfaces rather than smooth surfaces. In this manner, a surface may be bioactive due to its ability to stimulate cellular attachment and osteointegration.

In addition one or more surfaces of the anterior side 40, posterior side 50, or lateral sides 30 may also comprise a bioactive surface roughening 80, for example, as shown in FIG. 3A through FIG. 7B. Such surfaces may contact the remaining bone of vertebrae between the vertebral endplates in contact with the top surface 10 and bottom surface 20. The bone contacted by the one or more surfaces of the anterior side 40, posterior side 50, or lateral sides 30 comprises bone not removed through the corpectomy procedure. For example, the implant 1 may be inserted into a channel surgically created in the middle of a vertebrae, with the bony channel walls thereby contacting one or more surfaces of the anterior side 40, posterior side 50, or lateral sides 30 that have the bioactive surface roughening 80. In addition, the bony channel walls may also contact a bone graft material present in the hollow center 66 of the implant, which bone graft material may extend out from the one or more transverse apertures 70 that extend through the anterior side 40, posterior side 50, or lateral sides 30. The bone graft material may further stimulate or enhance fusion of the implant 1 with the vertebrae via the bony channel walls.

The bioactive surface roughening 80 (on any surface or portion of the implant) may be comprised of macro features, micro features, and nano features. For example, the bioactive surface roughening 80 may be obtained by combining separate macro processing, micro processing, and nano processing steps. Macro features include dimensions measured in millimeters (mm). Micro features comprise dimensions measured in microns (μm). Nano features include dimensions measured in nanometers (nm).

The shapes of the frictional surface protrusions of the bioactive surface roughening 80 may be formed using processes and methods commonly applied to remove metal during fabrication of implantable devices such as chemical, electrical, electrochemical, plasma, or laser etching; cutting and removal processes; casting; forging; machining; drilling; grinding; shot peening; abrasive media blasting (such as sand or grit blasting); and combinations of these subtractive processes. Additive processes such as welding, thermal, coatings, sputtering, and optical melt additive processes are also suitable. The resulting surfaces either can be random in the shape and location of the features or can have repeating patterns. This flexibility allows for the design and production of surfaces that resist motion induced by loading in specific directions that are beneficial to the installation process and resist the opposing forces that can be the result of biologic or patient activities such as standing, bending, or turning or as a result of other activities. The shapes of the surface features when overlapping increase the surface contact area but do not result in undercuts that generate a cutting or aggressively abrasive action on the contacting bone surfaces. Regular and repeating patterns are preferred.

These designed surfaces are composed of various sizes of features that, at the microscopic level, interact with the tissues and stimulate their natural remodeling and growth. At a larger scale these features perform the function of generating non-stressful friction that, when combined with a surgical technique that retains the most rigid cortical bone structures in the disc space, allow for a friction fit that does not abrade, chip, perforate, or compromise the critical endplate structures. The overlapping of the three feature sizes can be achieved using manufacturing processes that are completed sequentially and, therefore, do not remove or degrade the previous method.

The first step in the process may be mechanical (e.g., machining though conventional processes) or chemical bulk removal, for example, to generate macro features. The macro features may be of any suitable shape, for example, roughly spherical in shape, without undercuts or protruding tooth-like edges. Other shapes are possible, such as ovals, polygons (including rectangles), cones, triangles, and other shapes. These features may be at least partially overlapped with the next scale (micro) of features using either chemical or mechanical methods (e.g., $AlO_2$ blasting) in predetermined patterns which also do not result in undercuts or protruding sharp edges. The third and final process step is completed through more mild (less aggressive) etching (e.g., HCl acid etching) that, when completed, generates surface features in both the micro and nano scales over both of the features generated by the two previous steps. The nano layer dictates the final chemistry of the implant material.

Figure 8:
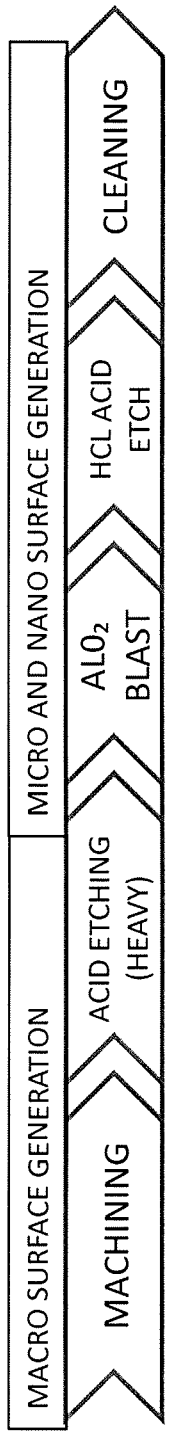
FIG. 8 illustrates process steps that can be used to form macro-, micro-, or nano-scale surface features and structures.

FIG. 8 illustrates one set of process steps that can be used to form the bioactive surface roughening 80. First, the implant 1 is machined, for example, from a bar stock comprising titanium, and a rough clean may be provided to remove any contaminants from machining. Second, particular surfaces of the implant 1 may undergo a heavy acid etching (e.g., masked etching). Next, particular surfaces of the implant 1 may undergo an abrasive blast, for example, using an alumina abrasive. The surfaces of the implant 1 may also undergo another acid etch, for example, with a solution comprising hydrochloric acid. Finally, the surfaces of the implant 1 may undergo a cleaning (e.g., with water and optionally a detergent). As illustrated, there may be some overlap in the processes that can be applied to form each of the three types of features (macro, micro, and nano). For example, acid etching can be used to form the macro features, then the same or a different acid etching process can be used to form the micro features.

The macro features of the bioactive surface roughening 80 are relatively large features (e.g., on the order of millimeters). The macro features may be formed from subtractive techniques (e.g., mechanical or chemical bulk removal, for example) or additive techniques (e.g., deposition). Preferably, the macro features are formed by subtractive techniques, which remove portions of the surface (e.g., from the base material that was used to form the implant 1). Suitable subtractive techniques may include, for example, machining (e.g., machine tools, such as saws, lathes, milling machines, and drill presses, are used with a sharp cutting tool to physically remove material to achieve a desired geometry) or masked etching (e.g., portions of the surface are protected by a masking material which resists etching and an etching substance is applied to unmasked portions). The patterns may be organized in regular repeating patterns, and optionally overlap each other. In a preferred embodiment, the macro features may be formed in three, sequential steps.

The macro features may be produced by a heavy masked etching process, for example. Before etching, the surface may be cleaned and optionally blasted with an abrasive (e.g., alumina) in the areas to be chemically textured. Certain areas may be masked in a pattern. The surface may then be chemically milled, for example, using a composition comprising hydrofluoric acid. The maskant and chemical milling may be repeated any number of times necessary to produce the desired pattern and etching depth. After the final etching process, the maskant may be removed and the part may be cleaned. The surface may also be passivated, for example, using an aqueous solution comprising nitric acid. The part may be cleaned and rinsed with water.

The macro features may be formed, for example, using three cut patterns. Specifically, a first cut pattern of the macro features may be formed. The "cut 1" features of the first cut pattern may cover about 20% of the total area of the surface, for example, leaving about 80% of the original surface remaining. The range of these percentages may be about ±20%, preferably ±10%, and more preferably about ±5%. The "cut 1" features of the first cut pattern do not have any undercuts. In one embodiment, these "cut 1" features have the smallest diameter and greatest depth of the macro features that are formed during the sequential steps.

A second cut pattern of the macro features may be formed in the surface. Together, the "cut 1" features of the first cut pattern and the "cut 2" features of the second cut pattern may cover about 85% of the total area of the surface, for example, leaving about 15% of the original surface remaining. The range of these percentages may be about ±10% and preferably ±5%. In an embodiment of the invention, these "cut 2" features have both a diameter and a depth between those of the "cut 1" and "cut 3" features of the macro features that are formed during the first and third steps of the process of forming the macro features of the bioactive surface roughening 80.

A third cut pattern of the macro features may be formed in the surface. Together, the "cut 1" features of the first cut pattern, the "cut 2" features of the second cut pattern, and the "cut 3" features of the third cut pattern may cover about 95% of the total area of the surface, for example, leaving about 5% of the original surface remaining. The range of these percentages may be about ±1%. In an embodiment of the invention, these "cut 3" features may have the largest diameter and least depth of the macro features that are formed during the sequential process steps.

After the macro features are formed, additional process steps may be sequentially applied, in turn, to form the micro surface features (e.g., on the order of micrometers) of the bioactive surface roughening 80. The micro features may also be formed from subtractive techniques (e.g., mechanical or chemical bulk removal, for example) or additive techniques (e.g., deposition). Preferably, the micro features are also formed by subtractive techniques.

In an exemplary embodiment, the micro features are removed by masked or unmasked etching, such as acid etching. For example, portions of the surface, including portions of the surface exposed by the macro step(s) described above, may be exposed to abrasive blasting, chemical etching, or both. In an exemplary embodiment, the micro process includes an acid etching, with a strong acid, such as hydrochloric acid (HCl), hydroiodic acid (HI), hydrobromic acid (HBr), hydrofluoric acid (HF), perchloric acid ($HClO_4$), nitric acid ($HNO_3$), and sulfuric acid ($H_2SO_4$). Preferably, the acid etching uses an aqueous solution comprising hydrochloric acid. The etching process may be repeated a number of times as necessitated by the amount and nature of the irregularities required for any particular application. Control of the strength of the etchant material, the temperature at which the etching process takes place, and the time allotted for the etching process allows fine control over the resulting surface produced by the process. The number of repetitions of the etching process can also be used to control the surface features.

By way of example, an etchant mixture of at least one of nitric acid and hydrofluoric acid may be repeatedly applied to a titanium surface to produce an average etch depth of about 0.53 mm. In another example, chemical modification of titanium can be achieved using at least one of hydrofluoric acid, hydrochloric acid, and sulfuric acid. In a dual acid etching process, for example, the first exposure is to hydrofluoric acid and the second is to a hydrochloric acid and sulfuric acid mixture. Chemical acid etching alone may enhance osteointegration without adding particulate matter (e.g., hydroxyapatite) or embedding surface contaminants (e.g., grit particles).

In one embodiment, the micro features are created by abrasive or grit blasting, for example, by applying a stream of abrasive material (such as alumina and sand) to the surface. In an exemplary embodiment, the micro features are created, at least partially, with an aqueous hydrochloric acid etching step and at least partially with an $AlO_2$ blasting step. Patterns may be organized in regular repeating patterns and optionally overlap each other. A After the micro features are formed, it is possible that less than about 3% of the original surface remains. The range of that percentage may be about ±1%.

After the macro features and micro features are formed, additional process steps may be sequentially applied, in turn, to form the nano surface features (e.g., on the order of nanometers) of the bioactive surface roughening 80. The nano features may also be formed from subtractive techniques (e.g., mechanical or chemical bulk removal, for example) or additive techniques (e.g., deposition). Preferably, the nano features are also formed by subtractive techniques.

In an exemplary embodiment, the nano features are removed by masked or unmasked etching. For example, portions of the surface, including portions of the surface exposed by the macro and micro steps described above, may be exposed to a chemical etching. In an exemplary embodiment, the nano process also includes an acid etching, with a strong or weak acid, such as hydrochloric acid (HCl), hydroiodic acid (HI), hydrobromic acid (HBr), hydrofluoric acid (HF), perchloric acid ($HClO_4$), nitric acid ($HNO_3$), and sulfuric acid ($H_2SO_4$). The acid etching process for the nano step is preferably less aggressive than the acid etching process in the macro or micro steps. In other words, a less acidic, mild, or more diluted acid may be selected. In an exemplary embodiment, the nano features are created, at least partially, with an aqueous hydrochloric acid etching step.

As an example, the nano features (or micro features) may be formed by preparing an acid solution comprising hydrochloric acid, water, and titanium; applying the acid solution to the surface; removing the acid solution by rinsing with water; and heating and subsequently cooling the surface.

The acid solution may be prepared using any suitable techniques known in the art. For example, the acid solution may be prepared by combining hydrochloric acid and water, simultaneously or sequentially. The aqueous hydrochloric acid solution may optionally be heated, for example, to a temperature of about 150-250° F. (66-121° C.), preferably about 200-210° F. (93-99° C.), and most preferably about 205° F. (96° C.). The titanium may be seeded (e.g., added) in the aqueous hydrochloric acid solution or may already be present from titanium previously removed from at least one surface of the implant, for example, in a continuous manufacturing process. The solution may optionally be cooled. The acid solution may comprise a concentration of 20-40% hydrochloric acid, preferably about 25-31% hydrochloric acid, and more preferably about 28% hydrochloric acid, based on the total weight of the solution.

It is contemplated that the nano features may also be created by the abrasive or grit blasting, for example, described for the micro processing step. Patterns may be organized in regular repeating patterns and optionally overlap each other. The nano features may also be achieved by tumble finishing (e.g., tumbling). The tumbling process may be wet (e.g., with a lubricant) or dry. After the nano features are formed, it is possible that less than about 1% of the original surface remains.

Any or each of the steps, including the macro, micro, or nano processing steps, may be accompanied by a cleaning step. In addition, the part may be cleaned once the processing steps are complete. For example, the part may be washed in an aqueous environment under agitation and heat with or without a detergent. Following washing, the part may be dried, for example with hot air, heating in a dry oven, or both.

The process steps described in this document can be adjusted to create a mixture of depths, diameters, feature sizes, and other geometries suitable for a particular implant application. The orientation of the pattern of features can also be adjusted. Such flexibility is desirable, especially because the ultimate pattern of the bioactive surface roughening 80 of the implant 1 should be oriented in opposition to the biologic forces on the implant 1 and to the insertion direction.

Several separate parameters can be used to characterize the surface roughness. Among those parameters are the average amplitude, Ra; the maximum peak-to-valley height, Rmax; and the mean spacing, Sm. Surface roughness may be measured using a laser profilometer or other standard instrumentation.

In addition to the parameters Ra, Rmax, and Sm mentioned above, at least two other parameters can be used to characterize the roughness of an implant surface. In summary, the five parameters are: (1) average amplitude, Ra; (2) average peak-to-valley roughness, Rz; (3) maximum peak-to-valley height, Rmax; (4) total peak-to-valley of waviness profile, Wt; and (5) mean spacing, Sm.

Figure 9:
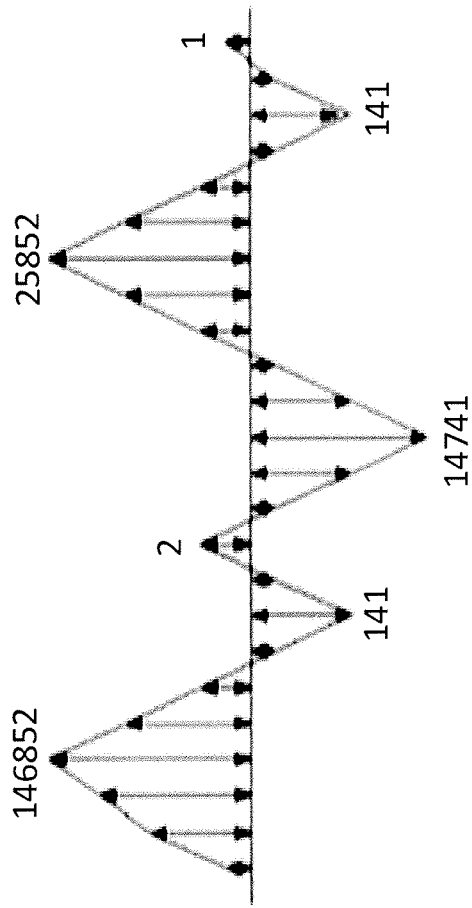
FIG. 9 graphically represents the average amplitude, Ra, of macro-, micro-, or nano-scale surface features and structures.

Average Amplitude Ra. Ra comprises an arithmetic average height. Mathematically, Ra may be computed as the average distance between each roughness profile point and the mean line. In FIG. 9, the average amplitude is the average length of the arrows.

In mathematical terms, this process can be represented by the following Formula I:

$$Ra = \frac{1}{n}\sum_{i=1}^{n}|y_i|$$

Figure 10:
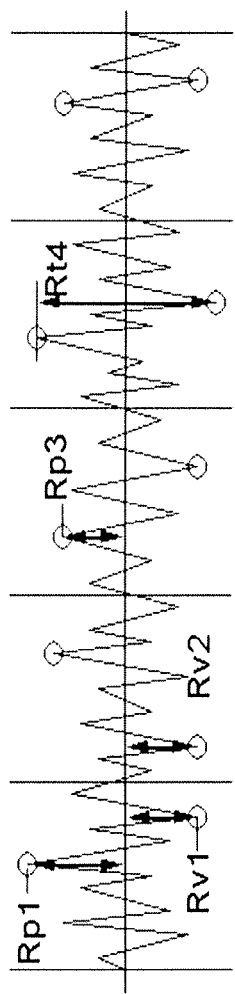
FIG. 10 graphically represents the average peak-to-valley roughness, Rz, of macro-, micro-, or nano-scale surface features and structures.

Average Peak-to-Valley Roughness Rz. The average peak-to-valley roughness, Rz, is defined by the ISO and ASME 1995 and later. Rz is based on one peak and one valley per sampling length. The RzDIN value is based on the determination of the peak-to-valley distance in each sampling length. These individual peak-to-valley distances are averaged, resulting in the RzDIN value, as illustrated in FIG. 10.

Figure 11:
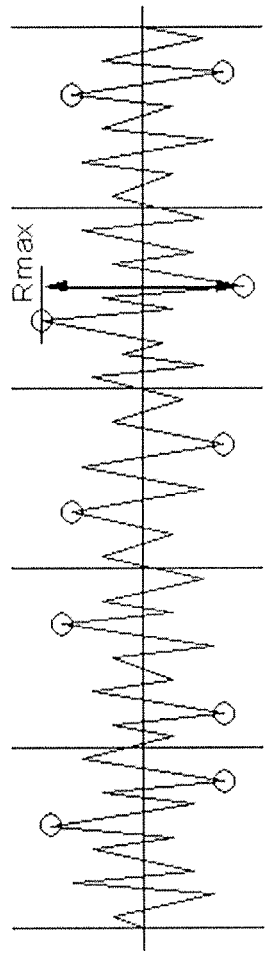
FIG. 11 graphically represents the maximum peak-to-valley height, Rmax, of macro-, micro-, or nano-scale surface features and structures.

Maximum Peak-to-Valley Height Rmax. The maximum peak-to-valley height, Rmax, comprises the maximum peak-to-valley distance in a single sampling length—as illustrated in FIG. 11.

Figure 12:
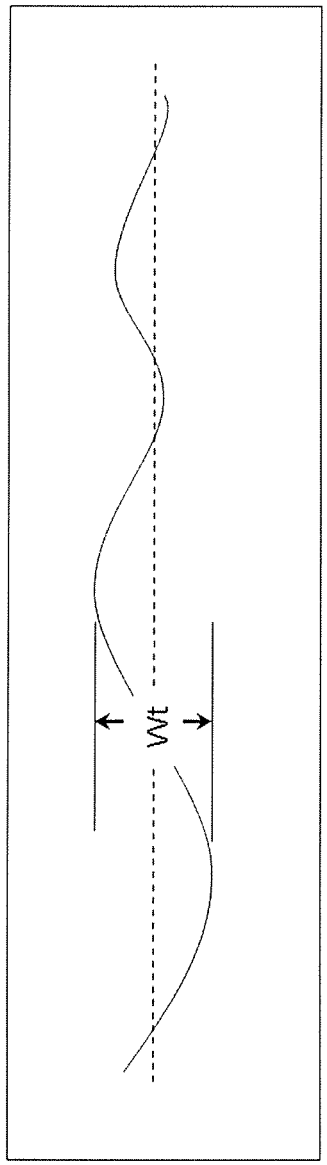

Total Peak-to-Valley of Waviness Profile Wt. The total peak-to-valley of waviness profile (over the entire assessment length) is illustrated in FIG. 12.

Figure 13:
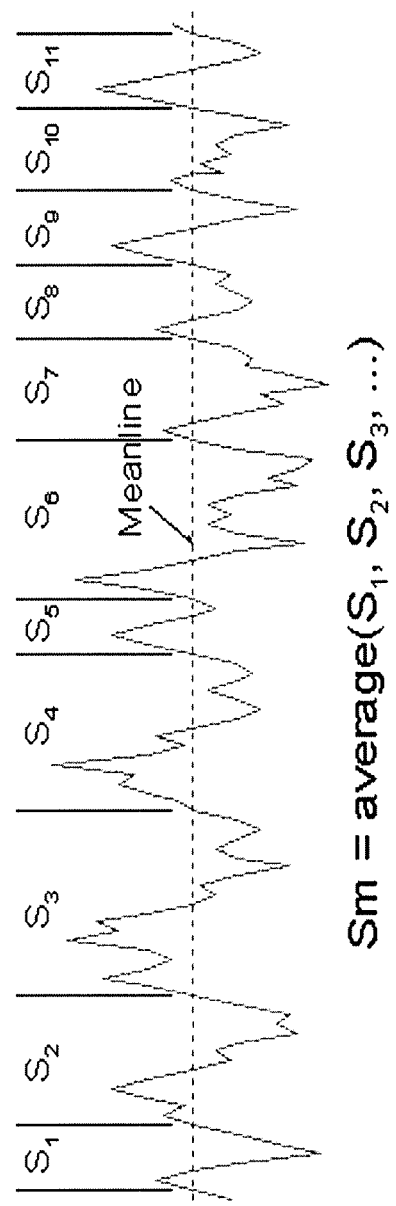
FIG. 13 graphically represents the mean spacing, Sm, of macro-, micro-, or nano-scale surface features and structures.

Mean Spacing Sm. The mean spacing, Sm, comprises the average spacing between positive mean line crossings. The distance between each positive (upward) mean line crossing is determined and the average value is calculated, as illustrated in FIG. 13.

The parameters Sm, Rmax, and Ra can be used to define the surface roughness following formation of each of the three types of features macro, micro, and nano. Such data are provided in Tables 1-3.

TABLE 1

Surface Feature Size and Roughness (Metric): Macro (μm)

| | Size (Sm) | Depth (Rmax) | Roughness (Ra) |
|---|---|---|---|
| Max. | 2,000 | 500 | 200 |
| Min. | 400 | 40 | 20 |
| Avg. | 1,200 | 270 | 110 |

TABLE 2

Surface Feature Size and Roughness (Metric): Micro (μm)

| | Size (Sm) | Depth (Rmax) | Roughness (Ra) |
|---|---|---|---|
| Max. | 400 | 40 | 20 |
| Min. | 20 | 2 | 1 |
| Avg. | 210 | 11 | 5.5 |

TABLE 3

Surface Feature Size and Roughness (Metric): Nano (μm)

| | Size (Sm) | Depth (Rmax) | Roughness (Ra) |
|---|---|---|---|
| Max. | 20 | 2 | 1 |
| Min. | 0.5 | 0.2 | 0.01 |
| Avg. | 10.25 | 1.1 | 0.505 |

The macro features for each of the three parameters may comprise the following preferred ranges (all measurements in microns). In some aspects, the macro mean spacing, Sm, is about 400 to about 2000 micrometers. More preferably, the macro mean spacing is about 750 to about 1750 micrometers, and more preferably, the macro mean spacing is about 1000 to about 1500 micrometers. In some aspects, the macro mean spacing is about 500 to about 1000 micrometers, about 600 to about 900 micrometers, about 700 to about 1000 micrometers, about 750 to about 1200 micrometers, about 800 to about 1300 micrometers, about 900 to about 1300 micrometers, about 1000 to about 1300 micrometers, about 1100 to about 1300 micrometers, about 1100 to about 1400 micrometers, about 1150 to about 1250 micrometers, about 1150 to about 1350 micrometers, about 1200 to about 1500 micrometers, or about 1200 to about 1400 micrometers. In some aspects, the macro peak-to-valley height, Rmax, is about 40 to about 500 micrometers. More preferably, the macro peak-to-valley height is about 150 to about 400 micrometers, and more preferably, about 250 to about 300 micrometers. In some aspects, the macro mean peak-to valley height is about 100 to about 450 micrometers, about 200 to about 400 micrometers, about 200 to about 300 micrometers, about 260 to about 280 micrometers, about 250 to about 350 micrometers, about 260 to about 320 micrometers, or about 270 to about 300 micrometers. In some aspects, the macro average amplitude, Ra, is about 20 to about 200 micrometers. More preferably, the macro average amplitude is about 50 to about 150 micrometers, and more preferably about 100 to about 120 micrometers. In some aspects, the macro average amplitude is about 80 to about 180 micrometers, about 90 to about 160 micrometers, about 90 to about 140 micrometers, about 100 to about 150 micrometers, about 100 to about 130 micrometers, about 105 to about 125 micrometers, or about 105 to about 115 micrometers.

The micro features for each of the three parameters may comprise the following preferred ranges (all measurements in microns). In some aspects, the micro mean spacing, Sm, is about 20 to about 400 micrometers. More preferably, the micro mean spacing is about 100 to about 300 micrometers, and more preferably, the macro mean spacing is about 200 to about 220 micrometers. In some aspects, the micro mean spacing is about 50 to about 350 micrometers, about 75 to about 350 micrometers, about 75 to about 300 micrometers, about 100 to about 325 micrometers, about 100 to about 250 micrometers, about 120 to about 220 micrometers, about 150 to about 250 micrometers, about 180 to about 240 micrometers, about 190 to about 230 micrometers, or about 205 to about 215 micrometers. In some aspects, the micro peak-to-valley height, Rmax, is about 2 to about 40 micrometers. More preferably, the micro peak-to-valley height is about 5 to about 25 micrometers, and more preferably, about 6 to about 16 micrometers. In some aspects, the micro mean peak-to valley height is about 0.5 to about 50 micrometers, about 1 to about 45 micrometers, about 1 to about 40 micrometers, about 1 to about 30 micrometers, about 1 to about 20 micrometers, about 1 to about 15 micrometers, about 2 to about 50 micrometers, about 2 to about 30 micrometers, about 2 to about 25 micrometers, about 3 to about 40 micrometers, about 3 to about 30 micrometers, about 4 to about 40 micrometers, about 4 to about 30 micrometers, about 5 to about 40 micrometers, about 5 to about 30 micrometers, about 7 to about 20 micrometers, about 7 to about 15 micrometers, about 8 to about 14 micrometers, or about 9 to about 13 micrometers. In some aspects, the micro average amplitude, Ra, is about 1 to about 20 micrometers. More preferably, the micro average amplitude is about 1 to about 10 micrometers, and more preferably about 3 to about 7 micrometers. In some aspects, the micro average amplitude is about 0.5 to about 30 micrometers, about 0.5 to about 25 micrometers, about 1 to about 15 micrometers, about 1 to about 10 micrometers, about 1 to about 9 micrometers, about 1 to about 7 micrometers, about 2 to about 9 micrometers, or about 4 to about 7 micrometers.

The nano features for each of the three parameters may comprise the following preferred ranges (all measurements in microns). In some aspects, the nano mean spacing, Sm, is about 0.5 to about 20 micrometers. More preferably, the nano mean spacing is about 5 to about 15 micrometers, and more preferably, the macro mean spacing is about 8 to about 12 micrometers. In some aspects, the nano mean spacing is about 0.1 to about 30 micrometers, about 0.25 to about 25 micrometers, about 0.5 to about 15 micrometers, about 0.5 to about 13 micrometers, about 1 to about 250 micrometers, about 1 to about 20 micrometers, about 1 to about 150 micrometers, about 2 to about 18 micrometers, about 2 to about 12 micrometers, about 7 to about 14 micrometers, or about 9 to about 11.5 micrometers. In some aspects, the nano peak-to-valley height, Rmax, is about 0.2 to about 2 micrometers. More preferably, the nano peak-to-valley height is about 0.5 to about 1.5 micrometers, and more preferably, about 0.8 to about 1.4 micrometers. In some aspects, the nano mean peak-to valley height is about 0.05 to about 5 micrometers, about 0.1 to about 3 micrometers, about 0.1 to about 2 micrometers, about 0.1 to about 1.5 micrometers, about 0.1 to about 0.4 micrometers, about 0.2 to about 3 micrometers, about 0.2 to about 2.5 micrometers, about 0.2 to about 1.8 micrometers, about 0.6 to about 1.6 micrometers, about 0.7 to about 1.5 micrometers, or about 0.9 to about 1.3 micrometers. In some aspects, the nano average amplitude, Ra, is about 0.01 to about 1 micrometers. More preferably, the nano average amplitude is about 0.05 to about 0.75 micrometers, and more preferably about 0.3 to about 0.7 micrometers. In some aspects, the nano average amplitude is about 0.005 to about 2 micrometers, about 0.005 to about 1.5 micrometers, about 0.01 to about 0.75 micrometers, about 0.01 to about 1.1 micrometers, about 0.01 to about 0.9 micrometers, about 0.01 to about 0.07 micrometers, about 0.025 to about 0.75 micrometers, or about 0.04 to about 0.6 micrometers.

Figure 2B:
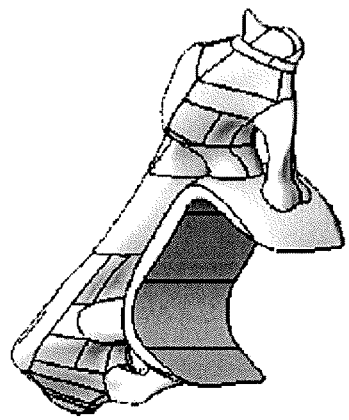
FIG. 2B shows a perspective view of a partial corpectomy of a vertebrae, with a portion of the vertebral endplate removed.
Figure 2C:
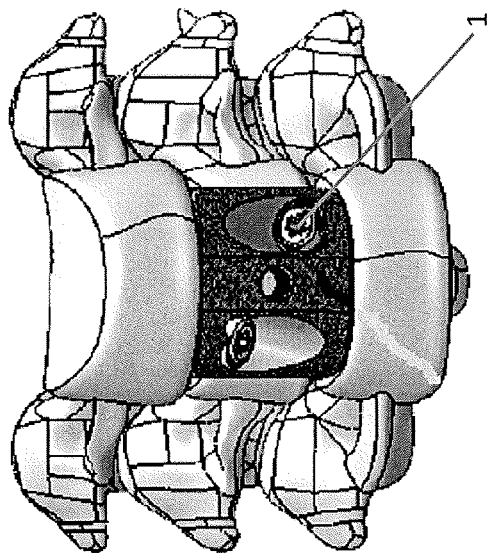
FIG. 2C shows an implant inserted into the channel of the vertebrae.
Figure 2A:
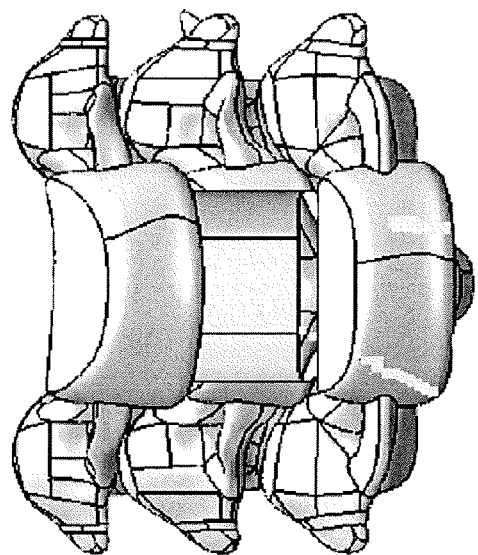
FIG. 2A shows an anterior view of a partial corpectomy of a vertebrae.

The implant 1 may be used in accordance with a corpectomy of vertebral body replacement procedure. The damaged or diseased portion of vertebral bone is removed, thereby forming a channel in one or more vertebrae (FIG. 2A and FIG. 2B). The channel preferably comprises bone that at least partially surrounds a void corresponding to the removed portion of vertebral bone (FIG. 2B). For replacement of a functional spinal unit, superior and inferior discs may also be removed, exposing vertebral endplate bone on the vertebrae above (upper vertebrae) and below (lower vertebrae) the vertebrae in which the channel was formed. The implant 1 may then be inserted into the channel, with the top surface 10 (comprising bioactive surface roughening 80) brought into contact with the inferior surface of the upper vertebrae, and the bottom surface (comprising bioactive surface roughening 80) brought into contact with the superior surface of the lower vertebrae. One or more of the anterior sidesurface 40, posterior sidesurface 50, or opposing lateral side 30 surfaces (comprising bioactive surface roughening 80) are brought into contact with the bone that at least partially surrounds the channel. Within the channel, the implant 1 may then be maneuvered into its intended position. Once the implant 1 is in its intended position within the bone channel, a screw may then be inserted through each screw aperture 46 and into adjacent bone (FIG. 2C). Once the implant 1 is in its intended position within the bone channel, a bone graft material, or additional bone graft material, may be placed in the hollow center 66. Bone graft material may be added via the one or more transverse apertures 70. Preferably, the bone graft material makes contact with the bone surrounding the channel. Preferably, the bone graft material makes contact with the endplate bone of the vertebrae above and the vertebrae below the vertebrae comprising the channel. The bone graft material may comprise cancellous autograft bone, allograft bone, demineralized bone matrix (DBM), porous synthetic bone graft substitute, bone morphogenic protein (BMP), or combinations thereof. The procedure is preferably carried out on a human being.

The invention is not limited to the embodiments described and exemplified above, but is capable of variation and modification within the scope of the appended claims.

What is claimed:

1. A corpectomy implant for replacing a functional spinal unit of a patient, wherein the functional spinal unit includes two adjacent vertebrae and an intervening disc, the implant comprising:
    a body that is generally oval-shaped in transverse cross section, has a height substantially the same as the height of the functional spinal unit to be replaced, the body comprising:
        an external top surface configured to contact a superior vertebra of the patient,
        an external bottom surface configured to contact an inferior vertebra of the patient, wherein the height of the body is measured from the top surface to the bottom surface,
        opposite external lateral sides extending between the external top surface and the external bottom surface,
        a substantially hollow center,
        an external anterior side extending between the external top surface and the external bottom surface, and including a transverse through aperture in fluid communication with the hollow center, the transverse through aperture having a height that is more than half the height of the body,
        an external posterior side opposite to the external anterior side, and extending between the external top surface and the external bottom surface and
        at least one vertical through aperture extending from the top surface to the bottom surface and defining a transverse rim on each of the top surface and the bottom surface, wherein a first portion of the transverse rim on the top surface is blunt and radiused along the top of each of the opposing external lateral sides and the top of the external posterior side, and a second portion of the transverse rim on the top surface, defining the external top surface, is not blunt and radiused around the at least one vertical aperture, and wherein a first portion of the transverse rim on the bottom surface is blunt and radiused along the bottom of each of the opposing external lateral sides and the bottom of the external posterior side, and a second portion of the transverse rim on the bottom surface, defining the external bottom surface, is not blunt and radiused around the at least one vertical aperture, and the second portions defining the top and bottom external surfaces, the external posterior side, and at least a portion of each of the external opposite lateral sides each have a roughened bioactive surface, wherein the roughened bioactive surface comprises a pattern of macro-scale, micro-scale, and nano-scale structures capable of facilitating bone growth,
    wherein the first portion of each of the transverse rims does not include any roughened surface, and the first portion on the top surface defines a blunt edge at a junction of the roughened bioactive surface of the second portion on the top external surface and the roughened bioactive surfaces of the external posterior side and the opposite external lateral sides, and the first portion on the bottom surface defines a blunt edge at a junction of the roughened bioactive surface of the second portion on the bottom external surface and the roughened bioactive surfaces of the external posterior side and the opposite external lateral sides, and
    wherein the body has a sharp edge at a junction of the external anterior side and the external top surface and at a junction of the external anterior side and the external bottom surface.

2. The implant of claim 1, wherein the body comprises titanium or titanium alloy.

3. The implant of claim 1, wherein the body comprises a polymer comprising polyetherether-ketone or ultra-high molecular weight polyethylene.

4. The implant of claim 1, wherein the body is a composite formed, in part, of metal and, in part, of a non-metal selected from polyetherether-ketone and ultra-high molecular weight polyethylene.

5. The implant of claim 1, wherein the posterior side has a generally tapered edge.

6. The implant of claim 1, wherein the implant comprises a lordotic angle adapted to facilitate alignment of the spine.

7. The implant of claim 1, further comprising bone graft material disposed in the substantially hollow center, wherein the bone graft material is cancellous autograft bone, allograft bone, demineralized bone matrix (DBM), porous synthetic bone graft substitute, bone morphogenic protein (BMP), or combinations thereof.

8. The implant of claim 1, wherein opening achieving the transverse through aperture achieves one or more of the following functions being adapted to engage a delivery device, facilitating delivery of bone graft material to the substantially hollow center, enhancing visibility of the implant, and providing access to the bone graft material.

9. The implant of claim 1, wherein the anterior side includes at least one transverse aperture has a substantially elliptical, D-shaped, triangular, or rectangular shapein communication with the hollow center.

10. The implant of claim 1, wherein the functional spinal unit is a cervical functional spinal unit.

11. The implant of claim 1, wherein the functional spinal unit is a lumbar functional spinal unit.

12. The implant of claim 1, wherein the macro-scale structures comprise a mean spacing from 400 micrometers to 2,000 micrometers, a peak-to-valley height from 40 micrometers to 500 micrometers, and an average amplitude from 20 micrometers to 200 micrometers.

13. The implant of claim 1, wherein the micro-scale structures comprise a mean spacing from 20 micrometers to 400 micrometers, a peak-to-valley height from 2 micrometers to 40 micrometers, and an average amplitude from 1 micrometer to 20 micrometers.

14. The implant of claim 1, wherein the nano-scale structures comprise a mean spacing from 0.5 micrometers to 20 micrometers, a peak-to-valley height from 0.2 micrometers to 2 micrometers, and an average amplitude from 0.01 micrometers to 1 micrometers.

15. A corpectomy implant for replacing a functional spinal unit of a patient, wherein the functional spinal unit includes two adjacent vertebrae and an intervening disc, the implant comprising:
  a body that is generally oval-shaped in transverse cross section and has a height substantially the same as the height of the functional spinal unit to be replaced, the body comprising:
    an external top surface configured to contact a superior vertebra of the patient,
    an external bottom surface configured to contact an inferior vertebra of the patient, wherein the height of the body is measured from the top surface to the bottom surface,
    opposite external lateral sides extending between the external top surface and the external bottom surface,
    a substantially hollow center,
    an external anterior side extending between the external top surface and the external bottom surface, and including a transverse aperture in fluid communication with the hollow center, the transverse aperture having a height that is more than half the height of the body,
    an external posterior side opposite to the external anterior sides, and extending between the external top surface and the external bottom surface, wherein the opposing external lateral sides and the external posterior side are solid,
    at least one vertical through aperture extending from the top surface to the bottom surface and defining a transverse rim on each of the top surface and on the bottom surface, wherein a first portion of the transverse rim on the top surface is blunt and radiused along the lop of each of the opposing external lateral sides and the top of the external posterior side, and a second portion of the transverse rim on the top surface, defining the external top surface, is not blunt and radiused around the at least one vertical aperture, and wherein a first portion of the transverse rim on the bottom surface is blunt and radiused along the bottom of each of the opposing external lateral sides and the bottom of the external posterior side, and a second portion of the transverse rim on the bottom surface, defining the external bottom surface, is not blunt and radiused around the at least one vertical aperture, and the second portions defining the top and bottom external surfaces, the external posterior side, and at least a portion of each of the external opposite lateral sides each have a roughened bioactive surface,
  the first portion of each of the transverse rims does not include any roughened surface, and the first portion on the top surface defines a blunt edge at a junction of the roughened bioactive surface of the second portion on the top external surface and the roughened bioactive surfaces of the external posterior side and the opposite external lateral sides, and the first portion on the bottom surface defines a blunt edge at a junction of the roughened bioactive surface of the second portion on the bottom external surface and the roughened bioactive surfaces of the external posterior side and the opposite external lateral sides, and
  the body having a sharp edge at a junction of the external anterior side and the top surface and at a junction of the external anterior side and the bottom surface, and
  wherein the roughened surface comprises a pattern of macro-scale, micro-scale, and nano-scale structures capable of facilitating hone growth, and wherein the macro-scale structures have an average mean spacing of from 400 micrometers to 2,000 micrometers, the micro-scale structures have an average mean spacing of from 20 micrometers to 400 micrometers, and the nano-scale structures have an average mean spacing of from 0.5 micrometers to 20 micrometers.

* * * * *